United States Patent
Vinogradov et al.

(10) Patent No.: US 9,119,577 B2
(45) Date of Patent: Sep. 1, 2015

(54) SPECIMEN COLLECTION DEVICE

(75) Inventors: Ilia V. Vinogradov, Elmhurst, IL (US); Tracey Powell, Chicago, IL (US); John Edward Steck, Round Lake, IL (US)

(73) Assignee: HOME ACCESS HEALTH CORPORATION, Hoffman Estates, IL (US)

( * ) Notice: Subject to any disclaimer, the term of this patent is extended or adjusted under 35 U.S.C. 154(b) by 1545 days.

(21) Appl. No.: 11/365,963

(22) Filed: Mar. 1, 2006

(65) Prior Publication Data

US 2007/0208275 A1    Sep. 6, 2007

(51) Int. Cl.
*A61B 5/15*    (2006.01)
*A61B 5/145*    (2006.01)

(52) U.S. Cl.
CPC ........... *A61B 5/1411* (2013.01); *A61B 5/14546* (2013.01); *A61B 2562/0295* (2013.01)

(58) Field of Classification Search
CPC .............. A61B 5/1405; A61B 5/1411; A61B 10/0045; A61B 2010/008; A61B 2562/0295; B01L 3/5027; B01L 3/50273
USPC ......... 600/573, 561, 405, 309, 398, 399, 579, 600/583, 584
See application file for complete search history.

(56) References Cited

U.S. PATENT DOCUMENTS

| | | | |
|---|---|---|---|
| 4,839,296 A | 6/1989 | Kennedy et al. | |
| 5,238,652 A * | 8/1993 | Sun et al. | 422/412 |
| 5,300,049 A * | 4/1994 | Hogan | 604/317 |
| 5,407,581 A * | 4/1995 | Onodera et al. | 210/654 |
| 5,435,970 A | 7/1995 | Mamenta et al. | |
| 5,935,775 A | 8/1999 | Savjani | |
| 5,978,466 A | 11/1999 | Quattrocchi | |
| 6,014,438 A | 1/2000 | Quattrocchi | |
| 6,016,345 A | 1/2000 | Quattrocchi | |
| 6,040,135 A | 3/2000 | Tyrrell | |
| 6,187,531 B1 | 2/2001 | Tyrrell | |
| 6,226,378 B1 | 5/2001 | Quattrocchi | |
| 6,524,533 B1 * | 2/2003 | Tyrrell | 422/102 |
| 7,294,502 B2 * | 11/2007 | Eckermann et al. | 435/287.1 |
| 7,300,627 B1 * | 11/2007 | Sun | 422/417 |
| 2004/0241752 A1 * | 12/2004 | Anderson et al. | 435/7.1 |

(Continued)

FOREIGN PATENT DOCUMENTS

| | | |
|---|---|---|
| EP | 0 419 196 A2 | 3/1991 |
| EP | 0 503 356 B1 | 10/1996 |
| WO | WO 00/44930 | 8/2000 |

OTHER PUBLICATIONS

Felix Wroblewski and John S. Ladue; Serum Glutamic Pyruvie Transaminase in Cardiac and Hepatic Disease; Proceedings of the Society for Experimental Biology and Medicine; Jan.-Apr. 1956, vol. 91, New York.

(Continued)

*Primary Examiner* — Adam J Eiseman
(74) *Attorney, Agent, or Firm* — Vedder Price P.C.

(57) ABSTRACT

Disclosed is a fluid collection device that comprises a housing having a normally obverse fluid receiving side and an opposing side. The fluid receiving side has an aperture for receiving a fluid and permitting deposition of the fluid into a fluid collector. The fluid collector is normally inclined to permit inclined fluid flow away from the aperture. Also disclosed is a kit that includes the fluid collection device, and various methods for use of the fluid collection device.

15 Claims, 6 Drawing Sheets

(56) References Cited

U.S. PATENT DOCUMENTS

2005/0186111 A1* 8/2005 Wang et al. .................. 422/56
2005/0266499 A1* 12/2005 Tan et al. .................... 435/7.1

OTHER PUBLICATIONS

Michael McGowan, Joseph D. Artiss, Donald R. Strandbergh, and Bennie Zak; A peroxidase-Coupled Method for the Colorimetic Determination of Serum Triglycerides; Journal of the American Association for Clinical Chemistry; vol. 29, No. 1, Jan. 1983.

Charles C. Allain, Lucy S. Poon, Cicely S.G. Chan, W. Richmond, and Paul C. Fu; Enzymatic Determination of Total Serum Cholesterol; Clinical Chemistry, vol. 20, No. 4, 1974.

Callum G. Fraser, Steven T. Cummings, Stephen P. Wilkinson, Ronald G. Neville, James D. E. Knox, Olga Ho, and Ronald S. MacWalter; Biological Variability of 26 Clinical Chemistry Analytes in Elderly People; Clinical Chemistry, vol. 35, No. 5, 1989.

M.D. Penney and G. Walters; Are osmolality measurements clinically useful?; Journals of Cllinical Biochemistry; vol. 24, Part 6 Nov. 1987.

Ravel, Richard; Clinical Laboratory Medicine; Sixth Edition, 1995, pp. 171-172, 405-413 and 417-420.

Erhardt, Juergen G et al.; Combined measurement of retinol and soluble transferring receptor (sTfR) in a single dired blood spot (DBS) stored at room temperature; Faseb Journal; vol. 16, No. 4, Mar. 20, 2002, pp. A247-A248, XP009019440; Annual Meeting of the Professional Research Scientists on Experimental Biology; New Orleans, Louisiana, USA; Apr. 20-24, 2002.

Erhardt, Juergen G et al.; Rapid and Simple Measurement of Retinol in Human Dried Whole Blood Spots; Journal of Nutrition; vol. 132, No. 2, Feb. 2002; pp. 318-321, XP002258787.

O'Brien J M et al.; Detection of Hepatitis C Antibody with At-Home Collection Kits Using an Innovative Laboratory Algorithm; Infectious Diseases in Clinical Practive; 2001 USA; vol. 10, No. 9, pp. 474-480; XP00115589.

* cited by examiner

SPECIMEN COLLECTION DEVICE

TECHNICAL FIELD

The invention is in the field of bodily fluid collection for testing. In particular, the invention is directed towards a collection device used to collect, separate, and preserve cell and cell-free fluid specimens for transport and medical testing.

BACKGROUND

Modem medical and wellness practices increasingly make use of self-administered tests and self-collection of test specimens. For example, a patient obtains a blood specimen, typically by pricking his or her finger, and allows the blood to wick onto a blood spot card. After the card has dried, the user then sends the blood spot card to a medical testing facility for testing.

The blood collection cards known in the art are suitable for use in the collection of whole blood specimens or plasma or serum for laboratory analysis, However, such collection devices have been unsatisfactory in the testing of bodily fluids when both cellular and fluid components are used.

For instance, diabetes treatment protocol indicates quantitative measurement of a patient's glucose in serum or plasma and glycated hemoglobin (A1c) in red blood cells. Whole blood collection device will provide hemoglobin result, but not glucose, while plasma/serum collection device will provide glucose, but not hemoglobin.

In addition, sample stability must be preserved through quick drying of the specimen collected to maximize the ability to analyze the sample in the testing facility or laboratory. Sample stability is adversely affected by the submission of a specimen that has not fully dried before being forwarded to a testing facility.

Another problem with certain heretofore devised blood collection devices is that a user of the device occasionally will inadvertently cause hemolysis of the blood specimen. In particular, certain blood collection devices are disclosed in U.S. patent application Ser. No. 10/706,321, filed Nov. 23, 2003; U.S. application Ser. No. 10/421,086, filed Apr. 23, 2003; and Provisional Application Ser. No. 60/374,629, filed Apr. 23, 2002. In accordance with the teachings of the foregoing applications, the specimen collection device includes an aperture by which a user may fluidically transfer blood from the user's finger to a blood collector. It has been observed that, although such specimen collection devices are useful in conjunction with the inventions disclosed and claimed in the foregoing patent applications, in some instances users of the device will press their finger onto the collector, thereby undesirably causing hemolysis of the sample. It is deemed desirable to provide a specimen collection device that mitigates against the foregoing.

Therefore, the invention seeks in preferred embodiments to present a device that provides for the collection, separation, and transport of bodily and other fluids, that is easy to use in both a medical and self-collection environment, and that will provide the testing facility or laboratory with a sufficient sample properly dried and ready for testing. In highly preferred embodiments, the invention seeks to provide a device that allows for the separation of blood cells from a fluid component of blood, and in which a user's finger or other body portion does not directly contact the fluid collector during collection of the device.

SUMMARY

In an aspect of the invention, a fluid collection device that comprises a housing having a normally obverse fluid receiving side and an opposite side having a support surface that defines a resting plane is provided. The fluid receiving side has an aperture for receiving a fluid and permitting deposition of the fluid onto a fluid collector. The fluid collector is inclined with respect to the resting plane to thereby gravitationally assist blood fluid in wicking away from the aperture. Preferably, the housing is provided with a plurality of air-permitting apertures. In one such aspect of the invention, the disposition of the collector in an inclined position in ordinary use and the provision of the housing with apertures have been found to provide improved collection properties when the fluid collected is blood from a finger prick.

It is contemplated in an aspect of the invention that the fluid to be collected is blood. In such case, the fluid collector is preferably an absorbent glass fibrous substrate that is coated with a saccharide, preferably a mono-or di-saccharide, such as L-xylose. The substrate is one that permits at least substantial separation of the blood cell component of blood cells from other portions of the blood via differential blood flow across the fluid collector, hence creating two separate specimens, one cell-free portion of blood and the other with blood cells. The invention also provides kits that include the fluid collection device and various methods that involve the fluid collection device, as set forth hereinbelow.

The various aspects of the invention are deemed particularly useful in the quantitative testing of blood, but are also deemed useful in conjunction with qualitative blood testing and with qualitative or quantitative testing of other fluids. The invention is deemed to find particular utility in conjunction with the inventions disclosed in U.S. patent application Ser. No. 10/706,321, filed Nov. 23, 2003; U.S. application Ser. No. 10/421,086, filed Apr. 23, 2003; and Provisional Application Ser. No. 60/374,629, filed Apr. 23, 2002. These prior applications are hereby incorporated by reference in their entireties.

Other aspects of invention are described in the drawing and the description set forth hereinbelow.

BRIEF DESCRIPTION OF THE FIGURES

In these Figures, terms of orientation (e.g. "top" and "bottom") are provided for convenience of reference and refer to the orientation of the fluid collection device in preferred usage during fluid collection. Such terms of orientation should not be construed as limiting the function, orientation, or use of the illustrated device.

DETAILED DESCRIPTION OF THE PREFERRED EMBODIMENTS

Figure 1:
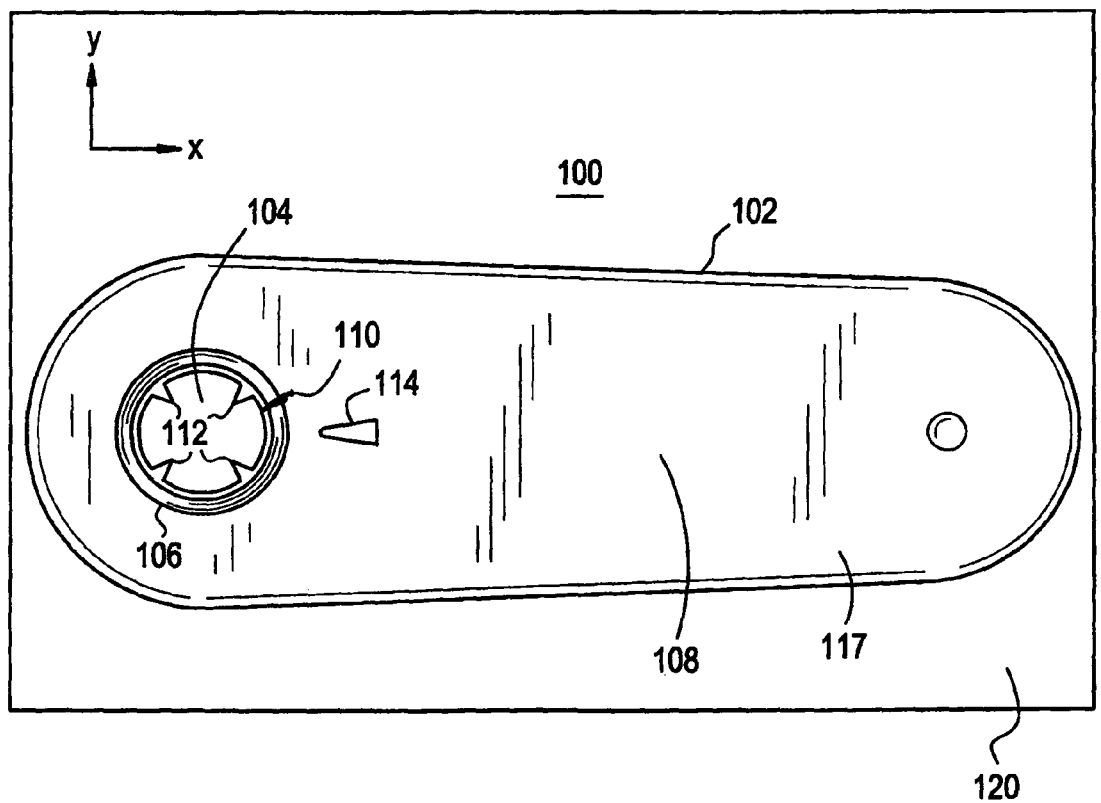
FIG. 1 is a plan view of the obverse side of the fluid collection device in accordance with an aspect of the invention.

In the following discussion, blood is described as the fluid of interest to be collected and tested by a testing facility. Those skilled in the art will realize that other fluids may be collected for testing using the collection device described herein. Numerous different tests may be preformed on a specific fluid. For for prostate specific antigen (PSA); alanineamino transferase (ALT); lipids, such as triglycerides; high density lipoprotein (HDL), and/or low density lipoprotein (LDL), using blood plasma/serum, on one hand, and glycohemoglobin using the red blood cells, on the other. The fluid collection device of the invention is deemed to be suitable for use with any other qualitative or quantitative test on the fluid collected as is permitted by the design of the collector. In one embodiment, the device is useful in conjunction with a test for antibodies for HIV or for the hepatitis virus. In another embodiment, the device is useful in conjunction with a test for blood glucose levels. In another embodiment, the device is useful in conjunction with a hemoglobin A1c (glycated hemoglobin) test. The foregoing tests are not mutually exclusive, and it is contemplated that multiple tests may be performed based on a specimen collected using a single device.

With reference to the figures, in particular FIGS. 1, 2, 3 and 4, a fluid collection device 100 generally includes a housing 102, and a fluid collector 302 (shown in FIG. 3) disposed within the housing 102. The fluid collection device 100 may be molded in separate parts that comprise mating top and bottom portions. For instance, the housing 102 of the fluid collection device 100 may comprise a top portion 117 and a bottom portion 119. The top portion 117 of housing 102 may have a normally obverse side 108 for receiving fluid, which is typically a bodily fluid and is most typically blood from a finger of a user obtained upon pricking the finger of the user.

Figure 5:
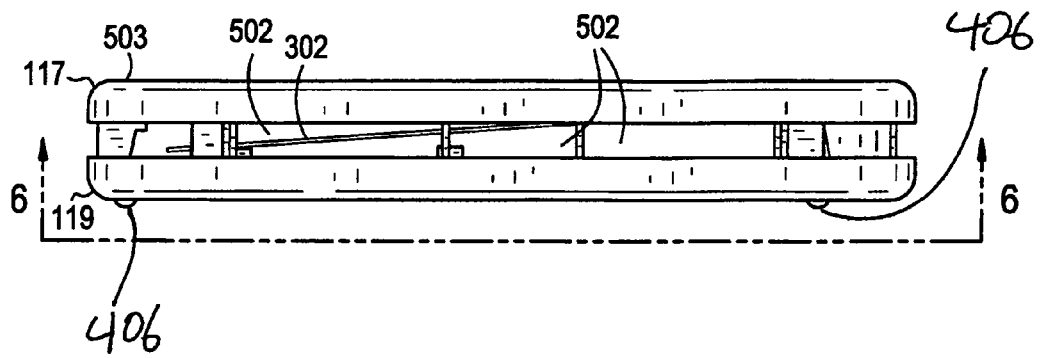
FIG. 5 is a side elevational view of the fluid collection device illustrated in FIG. 1 in accordance with an aspect of the invention.
Figure 6:
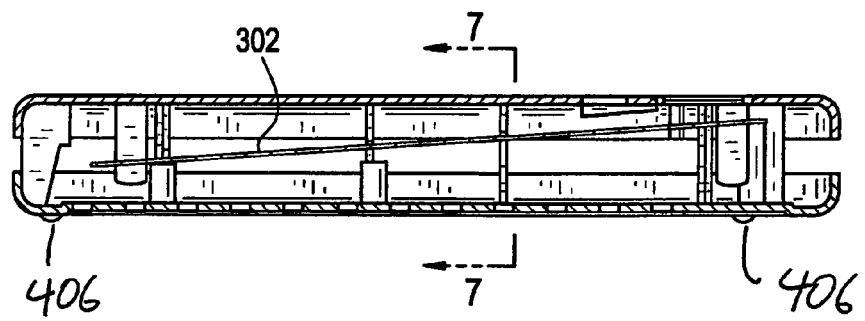
FIG. 6 is a side elevational view, partially cut-away, of the fluid collection device illustrated in FIG. 5 in accordance with an aspect of the invention.
Figure 7:
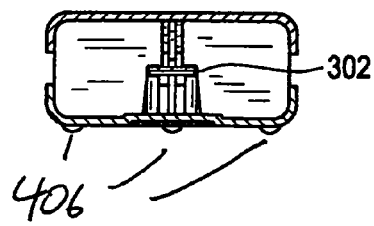
FIG. 7 is sectional view of the fluid collection device of FIG. 6 in accordance with an aspect of the invention.

The bottom portion 119 of the housing (shown in FIG. 4) has a bottom surface 403 that includes a plurality of depending nubs 406 (best shown in FIGS. 5-7) that together form a support surface that define a resting plane 120 (FIG. 1) for the fluid collection device 100. In the illustrated embodiment, the device is provided with three such depending nubs. In other embodiments, the resting plane may be defined by any continuous or discrete surface portions of the bottom surface 403. The designations "normally obverse" and "normally reverse" are used to describe orientations of the device in ordinary use and are not intended to limit the function, orientation, or use of the device.

The fluid collection device 100 also is provided with an aperture 104 (shown in FIGS. 1 and 2) for receiving fluid. As shown, the aperture 104 is formed in a dimple 106 on fluid receiving side 108. In an aspect of the invention, as shown, the aperture 104 has a perimeter 110 that is shaped to define a plurality of protrusions 112 which, along with the disposition of the aperture 104 in the dimple 106, serve to guide a finger of a user into the appropriate position for depositing blood into the fluid collection device 100. It is contemplated that the protrusions 112 may also assist in guiding blood droplets from the finger of the user into the fluid collection device 100 and onto the collector 302, and may also assist the user with the removal of the last drop of blood by providing a wiping surface. The protrusions also may provide a surface to assist in restarting blood flow when blood flow has stopped prematurely. Additionally, the protrusions 112 serve to impede contact by the user's finger with the collector 302 inside the fluid collection device 100. Such avoidance is deemed particularly useful in the collection of blood specimens.

The fluid collection device 100 may also include a specimen adequacy indicator window 114 (best shown in FIG. 1) which is remote from the aperture 104 and which is in a position to indicate when an adequate amount of fluid has been received from the user. The indicator window 114 may be an open aperture into the fluid collection device 100, but also be a closed window with a covering that is sufficiently clear to permit viewing of the fluid collector 302 inside the fluid collection device 100. The indicator window preferably has a perimeter that is arrow-shaped and that points to the fluid collection aperture, as shown in FIG. 1, to provide a visual indication to the user that blood should be directed to the aperture 104 and not to the indicator window 114. The fluid collector 302 is preferably sized such that a portion of the fluid collector 302 extends beyond the portion visible beneath the indicator window 114.

To assist in allowing drying of the fluid disposed on the collector 302, the housing 102 may be provided with numerous air permitting apertures. In an aspect of the invention, the sides of the assembled fluid collection device 100 may be provided with numerous apertures 502 (shown in FIG. 5) in the form of large, nearly continuous open spaces, and the bottom surface of the fluid collection device 100 may be provided with numerous apertures in the form of longitudinal transversely disposed slots 404. Instead of longitudinal transversely disposed slots 404, apertures having an asymmetrical shape may be provided. In ordinary use, the device will be placed on a flat supporting surface such as a table or counter, and the nubs 406 are provided to elevate the bottom surface 403 with respect to the flat supporting surface to permit air to flow to and through the slots 404.

Figure 2:
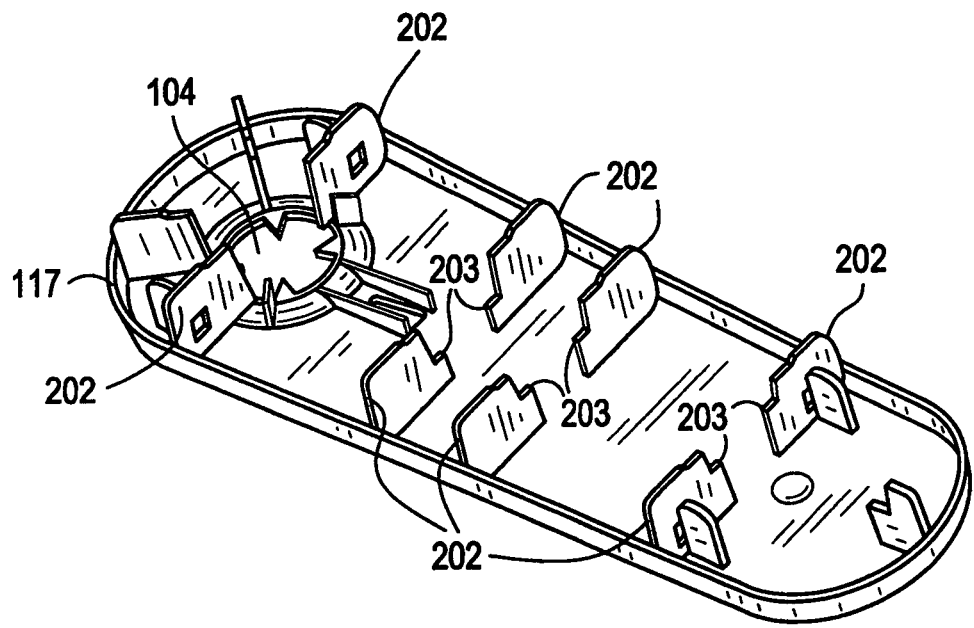
FIG. 2 is a perspective view of the back side of the receiving side of the fluid collection device illustrated in FIG. 1 in accordance with an aspect of the invention.
Figure 3:
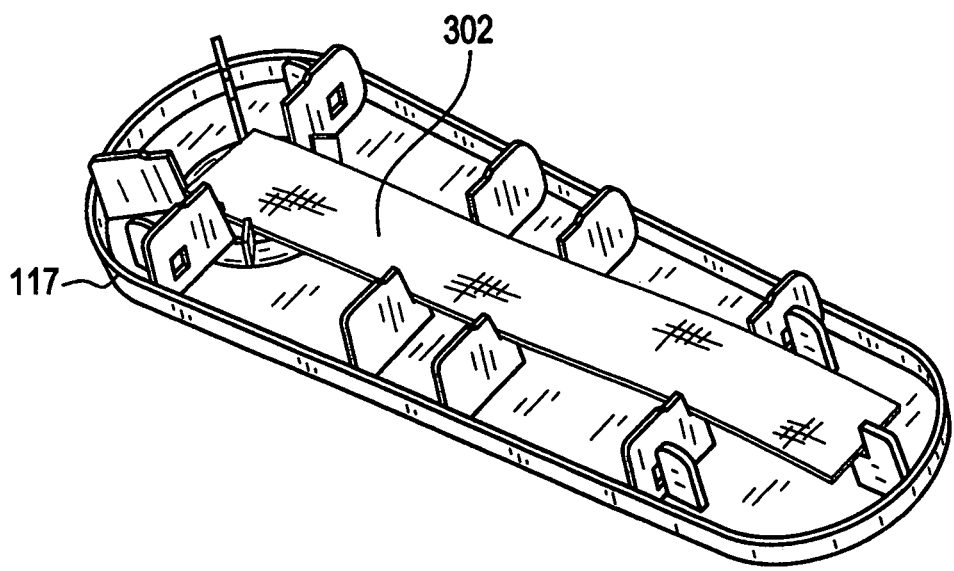
FIG. 3 is an additional perspective view of the back side of the receiving side with the fluid collector in accordance with an aspect of the invention.

The device may be molded with any suitable material, preferably a plastic material that is non-absorbent and that does not significantly promote blood coagulation. Most preferably, the material is polypropylene. The housing may be molded and assembled via any conventional methods. In FIG. 2, numerous ribs 202 are shown as projecting from the underside of top portion 117. The ribs 202 are shaped to mate with the bottom portion 119 of housing 102 to provide a snap-fit assembly. Those skilled in the art will realize that any suitable connection, such as a compression fit or an adhesive connection may be employed. Generally, the fit is of sufficient durability to deter disassembly of the device by the user, but not of sufficient durability to prevent or overly complicate disassembly by lab personnel.

In accordance with the invention, and as shown, in FIGS. 3, 5, 6, and 7, the fluid collection device 100 includes a fluid collector 302 that is inclined with respect to the resting plane 120 to thereby permit fluid to flow away from aperture 104 via gravitational fluid flow and via wicking of blood fluid.

Figure 4:
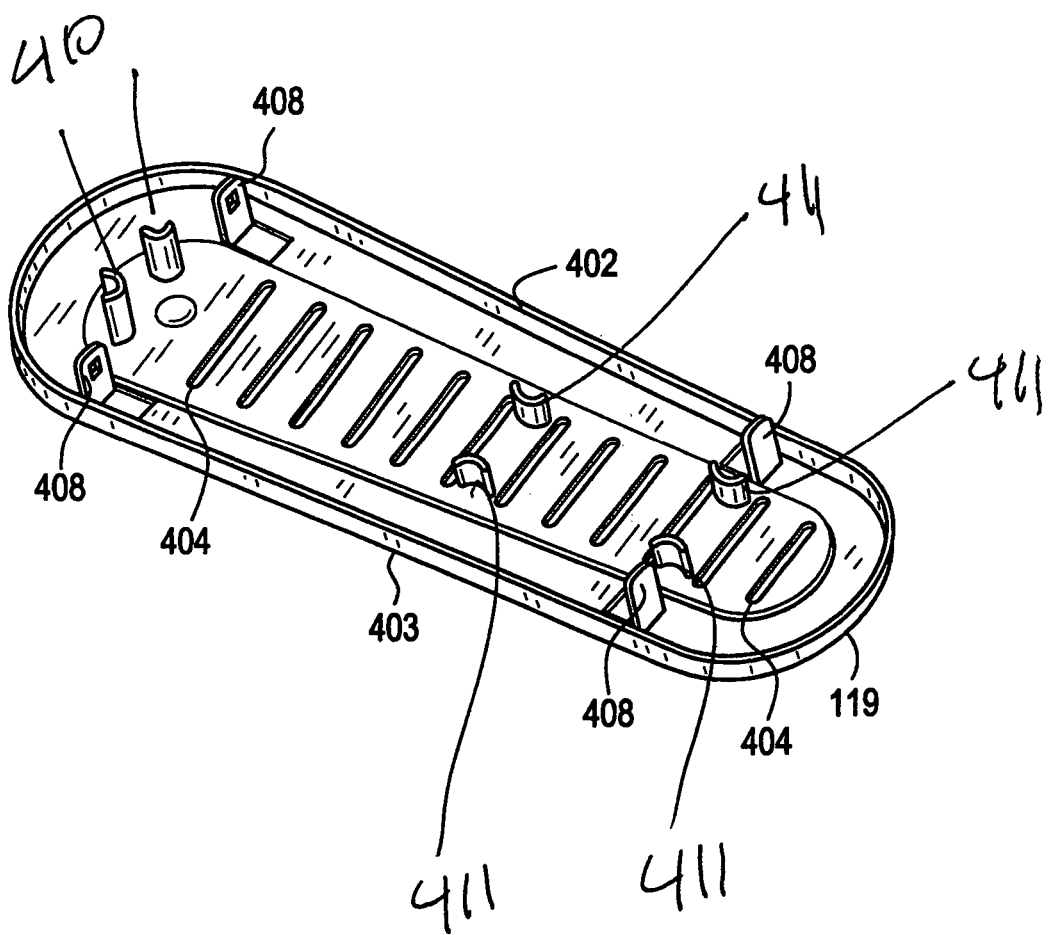
FIG. 4 is a plan view of the opposite side or bottom side the fluid collection device illustrated in FIG. 1 in accordance with an aspect of the invention.

As shown in FIG. 4, the lower portion 119 of the housing includes first and second supports 410, 411. The height of the first supports 410 relative to the reverse side of the fluid collector is large relative to that of the second supports 411, such that the fluid collector is maintained in an inclined position relative to the resting plane of the device. The ribs 202 of the upper portion may include ledge portions 203 which accommodate the fluid collector 302 in its inclined position. The distance between the ledge portions 203 and the obverse side of the device preferably diminishes as the distance from the aperture end of the fluid collection device 100 increases. Use of such supports 410,. 411 and ribs 202 provides for a relatively small solid contact area between the collector and the housing (relative to a collector supported along the entirety of its length) and a relatively large area of the collector that is exposed on both sides to ambient air. Preferably, a majority of the surface area of the supported side of the collector is exposed.

The fluid collector 302 may comprise an absorbent paper or, more preferably, a glass fiber substrate that is coated with a saccharide, preferably a mono or di-saccharide and most preferably xylose, such as L-xylose. The substrate should be one that permits at least substantial separation of the blood cell component of blood cells from other portions of the blood (i.e., a blood fluid component, which may be characterized as serum or plasma). It is believed that the saccharide component permits more effective recovery of the fluid components from the substrate sheet. The substrate may be coated only at the surface on one or both sides with the saccharide, but preferably the substrate is coated on internal surfaces as well as on the exterior surface. In its preferred embodiment, the substrate is coated with 10 mg L-xylose per square inch of strip by applying 180 µl of a 5% solution of xylose to the surface of the substrate (such that substantially all of the substrate is wetted) and drying the substrate. Preferably, the substrate is dried in a low-humidity environment at a temperature at or above 30 C.

The fluid collector 302 is separated from the finger of the user by the protrusions 112. In use, the user will not directly touch the fluid collector, but will cause fluid to contact the collector to thereby cause collection of a fluid specimen.

The glass fiber paper heretofore described comprises a mat of glass fibers that are at least substantially coated and bound with polyvinyl alcohol and further coated with L-xylose. One suitable known product is sold by Whatman under the designation GF/AVA. The fibers define a plurality of pores that have a pore size that, in preferred embodiments of the invention, is effective to at least substantially prevent lysing of red blood cells while permitting at least substantial separation of the blood fluid from the blood cell component of a blood specimen via differential wicking. Preferably, the average pore size defines a fluid removal rating, as this term is used in conjunction with filtration technology, of 1.7 micron. Any suitable substrate that provides such a pore size and that permits such substantial separation in the absence of blood cell lysing may be used in conjunction with the invention. In accordance with the disclosed embodiments, the wicking of blood is assisted by gravity in light of the inclined disposition of the collector. Blood does not flow over the upper, surface of the collector.

Figure 8:
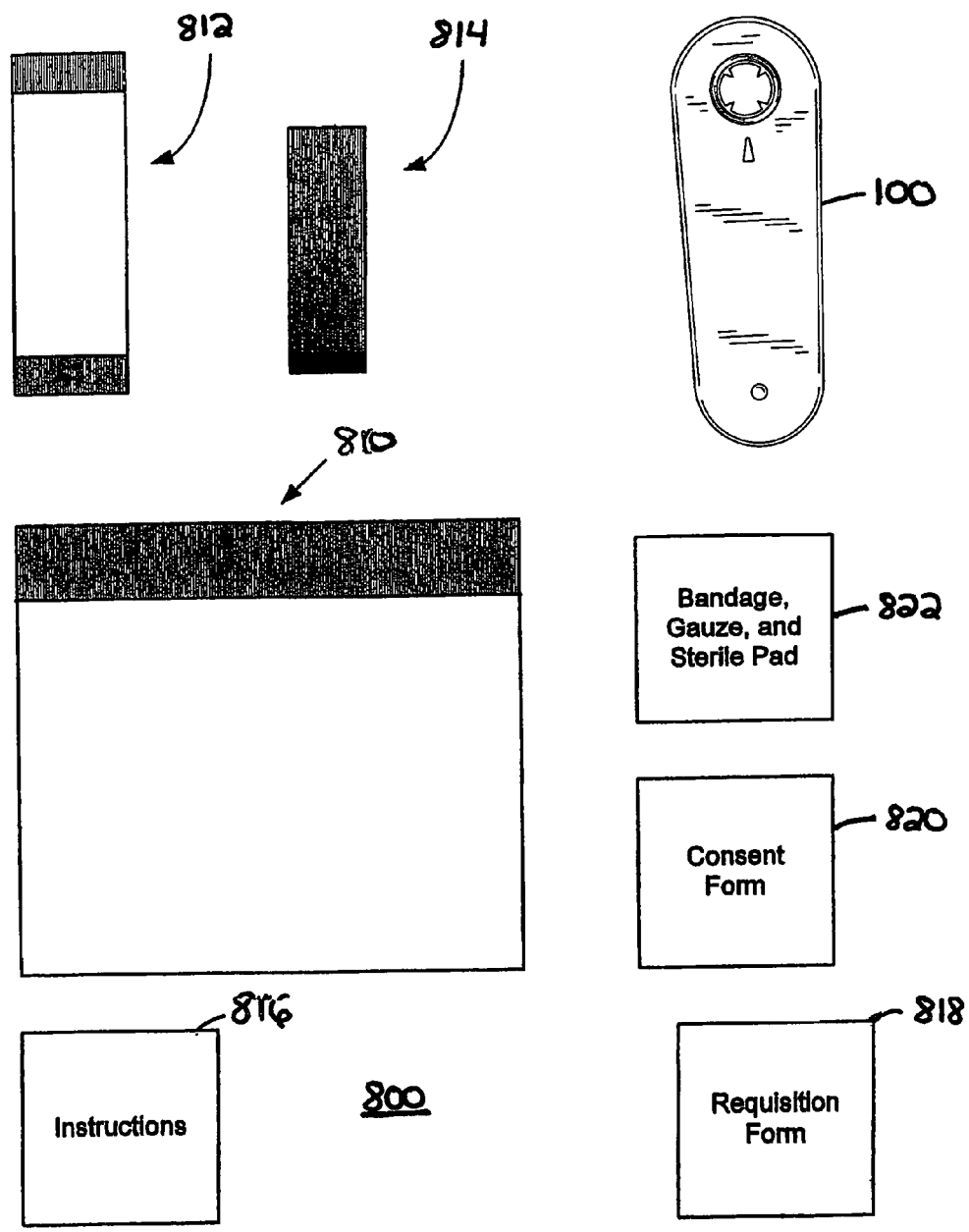
FIG. 8 schematically illustrates a kit containing the fluid collection device illustrated in FIG. 1 in accordance with an aspect of the invention.

The fluid collection device 100 may be furnished: by a health care provider to a patient for use in the presence of the provider, or may be furnished to a patient for use outside of the presence of medically trained personnel. By "patient" is contemplated any end user or consumer of the device, not necessarily a person under direct medical care, for whom it is desired to obtain a specimen. In either case, the fluid collection device is preferably provided as one component of a kit. As illustrated in FIG. 8, a kit 800 may include a fluid collection device 100, and numerous other components, some or none or all of which in practice may be included kit 800. Kit 800 may include a barrier pouch 810, a desiccant pouch 812, a lancet 814 (shown representationally), and instruction sheet 816 separate from kit 800. Kit 800 may also include a requisition form 818 and a consent form 820. The various forms may be separate or may be contained in a single document. In an aspect of the invention, kit 800 may include a mailing device (not shown) such as a preaddressed envelope with postage prepaid for sending the collection device to a testing facility or other appropriate facility. Kit 800 may further include a bandage, gauze pad, and alcohol pad (collectively represented as 822) for use with drawing blood from the patient. One, two, three, or more than three of the foregoing may be included with a fluid collection device to form a kit, as may any other suitable instrumentality.

The various components of the kit other than fluid collection device 100 may be standard components known in the art or otherwise found to be suitable for use in conjunction with the invention. For instance, the barrier pouch 810 should be a pouch that is effective in protecting the dried blood sample during shipping and that is sized to receive the fluid collection device 100 and the desiccant pouch 812. One suitable barrier material is sold by Caltex Plastics of Vernon, Calif. and comprises a multi-layer barrier film composed of 48 GA polyester film, 12 pound polyethylene, white ink, 0.0003 aluminum foil, 12 pound polyethylene and 1.6 mill linear low density polyethylene, the layers being bound together through the introduction of polyethylene. The pouch preferably is formed with at least one self-sealing device, such as a "zipper" disposed at least one end of the pouch. In one especially preferred embodiment, the pouch included a self-sealing "zipper" and a superceding heat seal at one end, and a heat seal at the other end of the device. The pouch is prepared by sealing the desiccant into the pouch, then heat-sealing the end of the pouch opposite the "zipper." When the pouch is used, the patient tears off and destroys the superceding heat seal above the zipper, inserts the collector, and closes the pouch using the self-sealing "zipper" device.

The desiccant pouch 812 should be a porous container that includes suitable desiccant effective to provide a dessicating protective effect on a blood fluid specimen, and to some extent to protect the integrity of the collection device during transport to the physician or patient. Any suitable desiccant material may be used in conjunction with the invention. One suitable desiccant is made by SudChemie of Balen, N. Mex. under part number 4286. This material comprises silica and clay disposed in admixture in a 5 gram pouch. Any other suitable desiccant may be used in conjunction with the invention.

Figure 9:
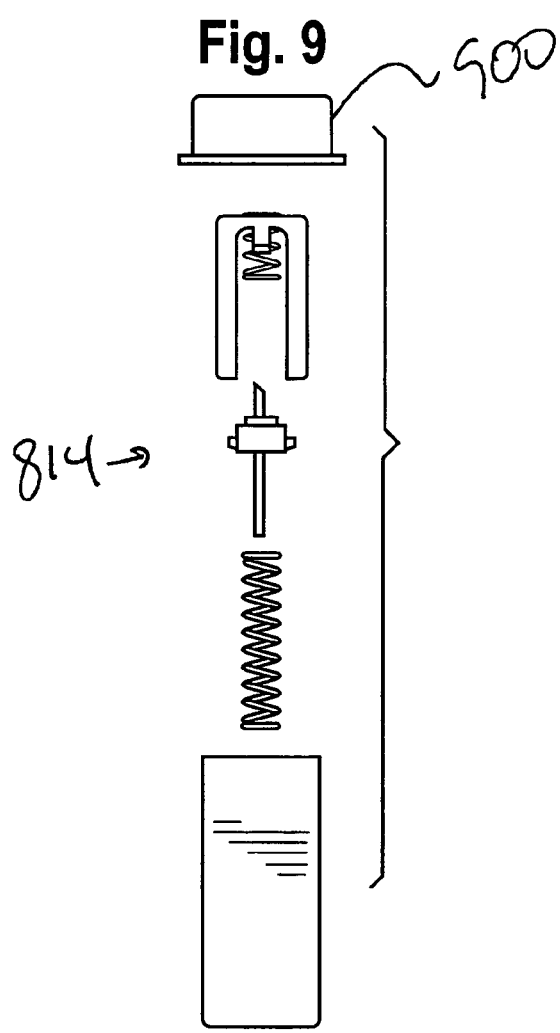
FIG. 9 is an exploded view of a lancet device deemed to be preferred for use in conjunction with the invention.
Figure 10:
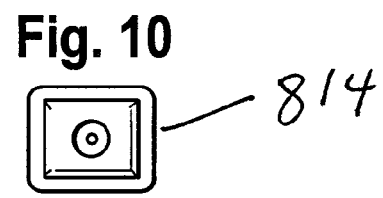
FIG. 10 is a top view of the lancet device illustrated in FIG. 9, shown with the covering cap removed.
Figure 11:
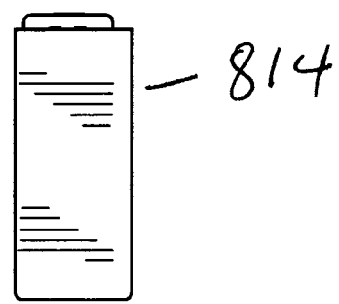
FIG. 11 is a side elevation of the lancet device illustrated in FIGS. 9 and 10.

Likewise, any suitable lancet may be employed in conjunction with the invention. The illustrated lancet 814, shown in more detail in FIGS. 9-11, comprises a blood-obtaining lancet such as that presently available from Surgilance. Pte Ltd, Singapore as the One-Step Plus Safety Lancet SLB 250. This device includes a single-use lancet that is spring-loaded to enable the lancet to sharply pierce a user's skin. A safety cap 901 also is provided. Any other suitable lancet may be used in conjunction with the invention.

The fluid collection device 100 and kit 800 have been described as comprising a single-gang device. In some embodiments of the invention, a device may comprise a dual-gang or other multi-gang device, with a plurality of separate fluid collectors. In such cases, each of the fluid collectors preferably is inclined as described herein with respect to fluid collector 302.

To collect a specimen, such as a blood specimen, the fluid collection device 100 is provided to a user, and the user (possibly with the assistance of a caregiver or other healthcare provider) places the user's finger into the dimple 106 after pricking of the user's finger with a suitable device, such as the lancet 814 discussed herein above. Blood will flow into the aperture 104 and onto the fluid collector 302. The patient (or healthcare provider) observes the indicator window 114, and, when the indicator window 114 reveals that sufficient blood has collected onto the fluid collector 302 to cause a change in color, the user's finger is removed. It is contemplated that other fluids and/or other sources of fluid (e.g., a toe) may be used in conjunction with the fluid collection device 100. In any event, the fluid collector will separate the blood specimen into a first portion that contains blood cells and a second portion that contains blood fluid and no blood cells (or a relatively small number of blood cells compared to the first portion). In practice, there will not be a sharp delineation between the first and second portions of the specimen; those skilled in the art will appreciate that the collector may be cleaved into two sections, one of which contains the bulk of the cells and the other of which contains relatively few or no cells. Upon collection of the specimen, the patient or health care provider then sends the device directly or indirectly to a testing facility.

Upon receipt by a testing facility, a portion of the fluid collector with blood cells and/or cell-free component may be excised and eluted, for instance, in accordance with the teachings of U.S. patent application Ser. No. 10/706,321, filed Nov. 23, 2003; U.S. application Ser. No. 10/421,086, filed Apr. 23, 2003; and Provisional Application Ser. No. 60/374,629, filed Apr. 23, 2002, or otherwise treated and examined. For test of blood cells, the other portion of the collector is excised and tested. In some embodiments of the invention, both portions of the collector are tested; with one or more tests being performed on the portion that contains blood cells and one or more tests being performed on the portion that contains fluid.

As described in U.S. patent application Ser. No. 10/706, 321, filed Nov. 23, 2003; U.S. application Ser. No. 10/421, 086, filed Apr. 23, 2003; and Provisional Application Ser. No. 60/374,629, filed Apr. 23, 2002, the fluid collection device 100 may be used in conjunction with numerous testing methodologies. For instance, the fluid collection device 100 may be particularly applicable in one or more remote testing methodologies wherein the sample is tested at a point of location remote from the point of collection. Thus, for example, a fluid collection device 100 or kit 800 may be used by a healthcare provider in the offices of the healthcare provider. The healthcare provider may administer the collection of fluid via use of the fluid collection device 100, and may send the fluid collection device 100 directly or indirectly to a testing facility for testing. In another aspect of the method of the invention, the fluid collection device 100 may be provided to a patient for use outside of the presence of a healthcare provider. This method may be particularly useful in conjunction with "home" testing methodologies, in particular, periodic testing for cholesterol. In accordance with this aspect of the invention, the patient is provided with a fluid collection device 100 from a distribution source, such as a retail store or via a healthcare provider. The patient is provided with instructions (such as instructions 816 in FIG. 8) that direct the patient to prick his or her finger, (such as with a lancet 814), to introduce sufficient sample into the fluid collection device 100, and to package the device and to send the device directly or indirectly to a testing facility.

Irrespective of whether the test is administered by a healthcare provider or is performed by a patient outside of the presence of a healthcare provider, the results of the test may be provided by a results providing facility. For instance, the results providing facility may maintain a database that correlates anonymous code numbers (by code "numbers" including alphanumeric designations or any suitable designations) with test results. The database in a results providing facility may be accessed remotely, such as via the Internet, via telephone, or the like, by either or both of the patient or healthcare provider. As described in the heretofore identified pending patent applications, the design of a testing methodology may be left to the discretion of those implementing the test and/or as may be as required by applicable law.

Thus, it is seen that the invention provides a device that provides for collection of bodily and other fluids that is easy to use by non-medical personnel, and that provides the testing facility or laboratory a sufficient sample that is properly dried upon shipment and ready for testing.

While particular embodiments to the invention have been described herein, the invention is not limited thereto, but to the contrary should be deemed defined by the full scope of the appended claims including equivalents as permitted by applicable law. No non-claimed subject matter should be deemed to limit the scope of the present invention. All references and prior and co-pending applications cited herein are hereby incorporated by reference in their entireties.

What is claimed is:

1. A blood fluid collection device comprising a housing having a normally obverse fluid receiving side and an opposing side having a support surface that defines a resting plane, the blood receiving side having an aperture for receiving blood and permitting deposition of the blood onto a blood collector disposed within and not integral to the housing made of paper or glass fiber substrate for the separation of blood cells, the blood collector being inclined with respect to and spaced apart from the resting plane and having normally upper portion disposed proximal said aperture thereby permitting blood to flow away from said aperture upon deposition of a blood onto said blood collector; wherein said opposing side of said housing is provided with a plurality of spaced apart supports for said blood collector, said blood collector being in the form of a strip having a supported side and an unsupported side, whereby a majority of the surface area of said supported side of said blood collector is exposed to ambient air.

2. A blood collection device according to claim 1, wherein the blood receiving side having a window disposed over a portion of said blood collector remote from said normally upper portion.

3. A blood collection device according to claim 1, wherein said opposing side of said housing is provided with a plurality of air permitting apertures.

4. A blood collection device according to claim 1, wherein said blood collector comprising an absorbent substrate.

5. A blood collection device according to claim 4, wherein said inclined surface of the blood collector comprises a substrate substantially bound with polyvinyl alcohol.

6. A blood collection device according to claim 5, wherein said fibers define a plurality of pores, the pores in said blood collector having a pore size effective to at least substantially prevent lysing of red blood cells while permitting at least substantial separation of a blood fluid component from blood cells via differential fluid flow.

7. A blood collection device according to claim 5, wherein said blood collector is coated with a saccharide.

8. A blood collection device according to claim 7, wherein said saccharide is L-xylose.

9. A blood collection device according to claim 1, wherein said aperture's disposed in a dimpled region of said blood receiving side.

10. A blood collection device according to claim 9, wherein the aperture defined by a perimeter that includes a plurality of protruding portions that extend inwardly in a radial direction from the perimeter.

11. A blood collection device according to claim 10, wherein said protruding portions being shaped and positioned to impede contact between the finger of a user and said blood collector but to allow blood to fluidically communicate with said blood collector.

12. A blood collection device according to claim 1, wherein said device including a specimen adequacy indicator window, said indicator window having a perimeter that is generally arrow-shaped and that points in the direction of the aperture for receiving blood.

13. A blood collection device according to claim 1, wherein the housing is made of a top portion and a bottom portion which includes the opposing side, wherein the top portion includes the aperture and the bottom portion includes a plurality of nubs extending away substantially perpendicularly from an exterior surface of the bottom portion for providing the resting plane.

14. A blood collection device according to claim 3, wherein the plurality of air permitting apertures comprise a plurality of longitudinally transversely disposed slots disposed on said opposing side of said housing.

15. A blood collection device according to claim 1, further comprising:

wherein said housing comprises a first end proximate said aperture and a second end disposed opposite the first end;

wherein said plurality of spaced apart supports for said blood collector further comprise a first plurality of supports located on said opposing side proximate said first end and a second plurality of supports located on said opposing side proximate said second end and said first plurality of supports extend farther from said opposing side than said second plurality of supports;

wherein a first plurality of ribs is located on said blood receiving side proximate said first end and a second plurality of ribs is located on said blood receiving side proximate said second end, and said second plurality of ribs extends farther from said blood receiving side than said first plurality of ribs; and wherein a first end of said strip is secured between said first plurality of supports and said first plurality of ribs and a second end of said strip is secured between said second plurality of supports and said second plurality of ribs, such that said supported side is adjacent to but separated from said opposing side and said unsupported side is adjacent to but separated from said blood receiving side.

* * * * *